US009439698B2

(12) United States Patent
Songer et al.

(10) Patent No.: US 9,439,698 B2
(45) Date of Patent: Sep. 13, 2016

(54) CABLE FIXATION DEVICE

(71) Applicant: Frontier Medical Devices, Inc., Gwinn, MI (US)

(72) Inventors: Matthew Songer, Marquette, MI (US); Fran Korhonen, Negaunee, MI (US); Jeff Mosteller, Skandia, MI (US); Wes Hanna, Marquette, MI (US); Branden Wainio, Negaunee, MI (US)

( * ) Notice: Subject to any disclaimer, the term of this patent is extended or adjusted under 35 U.S.C. 154(b) by 0 days.

(21) Appl. No.: 14/216,913

(22) Filed: Mar. 17, 2014

(65) Prior Publication Data

US 2015/0127003 A1    May 7, 2015

Related U.S. Application Data

(60) Provisional application No. 61/801,837, filed on Mar. 15, 2013.

(51) Int. Cl.
*A61B 17/82* (2006.01)
*A61B 17/88* (2006.01)
*A61B 17/84* (2006.01)

(52) U.S. Cl.
CPC .............. *A61B 17/82* (2013.01); *A61B 17/842* (2013.01); *A61B 17/8861* (2013.01); *A61B 17/8869* (2013.01); *A61B 17/8872* (2013.01); *A61B 17/8894* (2013.01); *Y10T 24/398* (2015.01); *Y10T 24/49* (2015.01)

(58) Field of Classification Search
CPC   A61B 17/82; A61B 17/842; A61B 17/8861; A61B 17/8869; A61B 17/8872; Y10T 24/398; Y10T 24/49
See application file for complete search history.

(56) References Cited

U.S. PATENT DOCUMENTS

| | | | |
|---|---|---|---|
| 3,111,945 A | 11/1963 | VonSolbrig | |
| 3,952,377 A | 4/1976 | Morell | |
| 4,889,110 A | 12/1989 | Galline et al. | |
| 4,966,600 A * | 10/1990 | Songer | A61B 17/8869 606/103 |
| 4,979,911 A | 12/1990 | Spencer | |
| 5,415,658 A * | 5/1995 | Kilpela | A61B 17/8861 606/297 |
| 5,536,270 A | 7/1996 | Songer et al. | |
| 5,649,927 A | 7/1997 | Kilpela et al. | |
| 5,772,663 A | 6/1998 | Whiteside et al. | |
| 5,964,769 A | 10/1999 | Wagner et al. | |
| 6,086,590 A | 7/2000 | Margulies et al. | |
| 6,277,120 B1 | 8/2001 | Lawson | |
| 6,436,099 B1 | 8/2002 | Drewry et al. | |
| 6,629,975 B1 | 10/2003 | Kilpela et al. | |
| 6,730,092 B2 | 5/2004 | Songer | |
| 6,994,725 B1 | 2/2006 | Goble | |

(Continued)

*Primary Examiner* — Larry E Waggle, Jr.

(57) ABSTRACT

Various forms of a cable fixation device, instrumentation, kit, and methods useful for repairing the skeletal system are introduced. The system utilizes a clamp housing fixing a butt end of a surgical cable therein. In an operative configuration the cable is looped around a damaged bone segment and reentered through a lock aperture in the clamp housing then through a collet and lock cap residing within the lock aperture. The cable loop and each aforementioned component comprise a central axis aligned within a single plane. A sliding interface situated between the lock cap and collet prevent twisting of the surgical cable. The locking mechanism is non-destructive to the cable despite repeated unlocking and relocking of the fixation device. The axis for tensioning of the cable is coincident with the locking axis. A counter torque instrument has a torsional input shaft generally perpendicular to the elongated axis of the instrument.

25 Claims, 13 Drawing Sheets

(56) References Cited

U.S. PATENT DOCUMENTS

| | | |
|---|---|---|
| 7,172,595 B1 | 2/2007 | Goble |
| 7,207,090 B2 | 4/2007 | Mattchen |
| 7,255,701 B2 | 8/2007 | Allen et al. |
| 8,128,627 B2 | 3/2012 | Justin et al. |
| 8,225,463 B2 | 7/2012 | Bourke et al. |
| 8,241,288 B2 | 8/2012 | Justin et al. |
| 8,246,655 B2 | 8/2012 | Jackson et al. |
| 8,496,659 B2 * | 7/2013 | Dell'oca ............... A61B 17/82 606/280 |
| 8,968,318 B2 * | 3/2015 | Dell'Oca ............... A61B 17/82 606/74 |
| 2006/0235401 A1 | 10/2006 | Baldwin et al. |
| 2007/0100345 A1 | 5/2007 | Fernandez |
| 2009/0082820 A1 | 3/2009 | Fielding et al. |
| 2010/0256612 A1 * | 10/2010 | Dell'Oca ............... A61B 17/82 606/1 |
| 2010/0305571 A1 | 12/2010 | Pratt et al. |
| 2010/0318137 A1 | 12/2010 | Stucki et al. |
| 2012/0310242 A1 | 12/2012 | Justin et al. |
| 2013/0018375 A1 | 1/2013 | Dell'Oca |

* cited by examiner

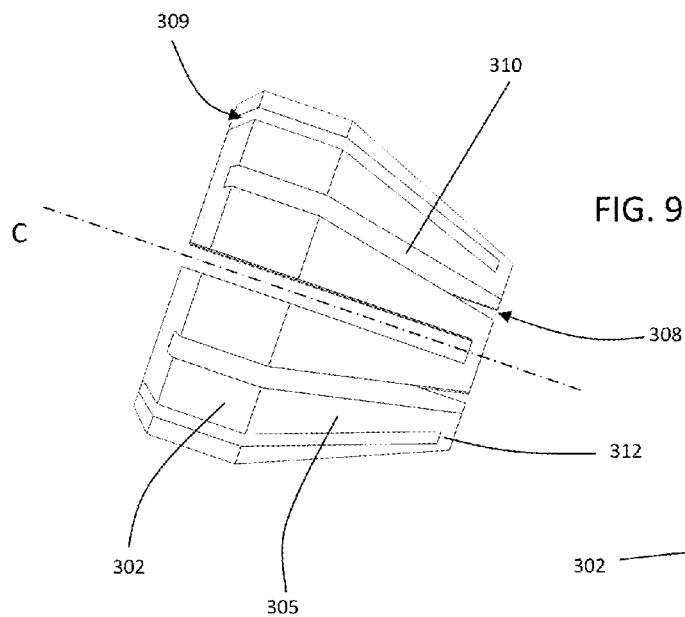
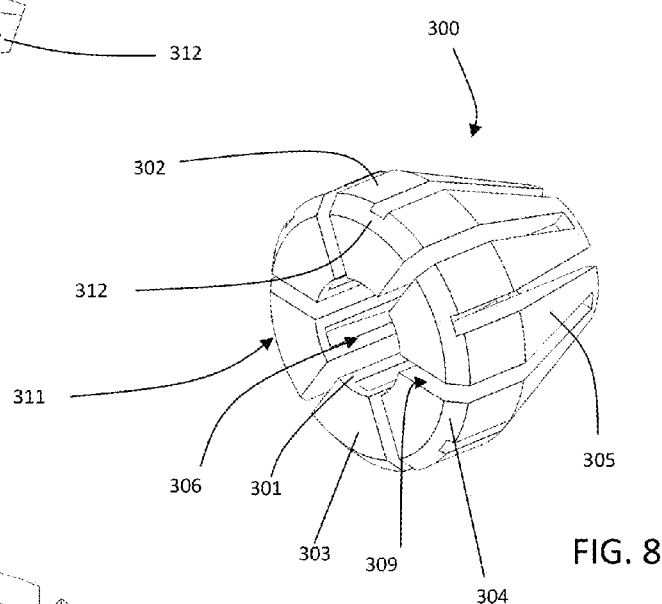
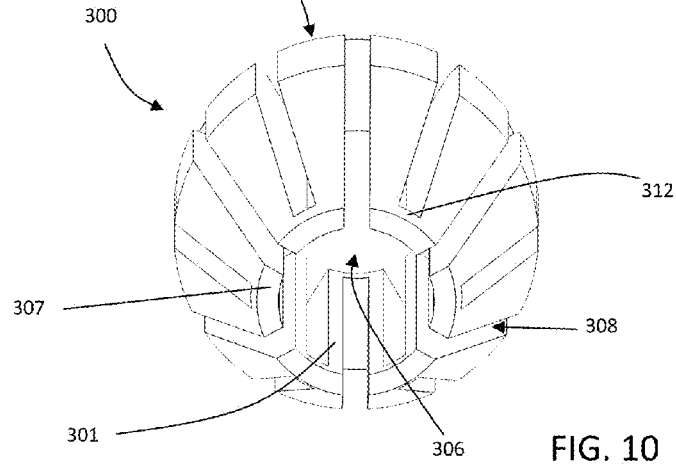
FIG. 9
FIG. 8
FIG. 10

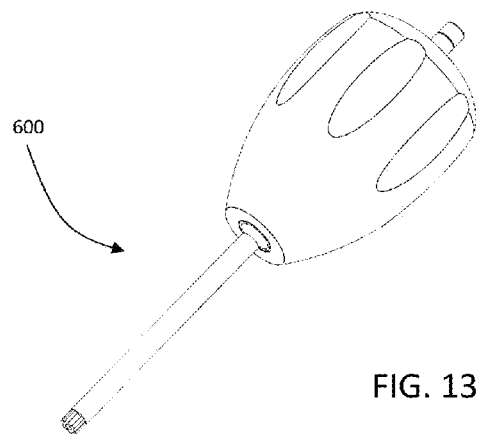
FIG. 13
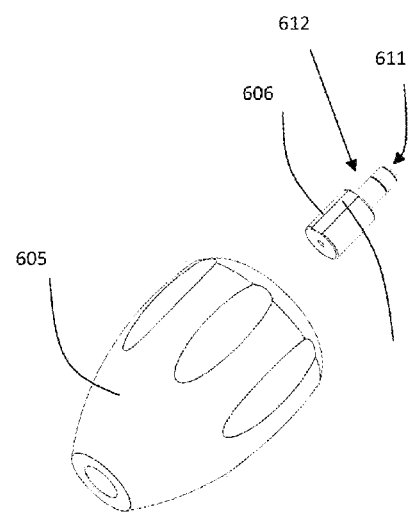
FIG. 14
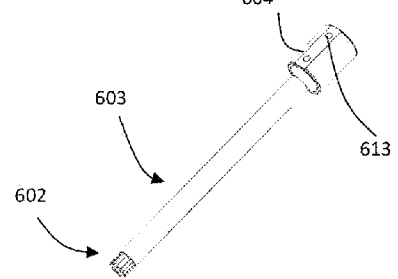
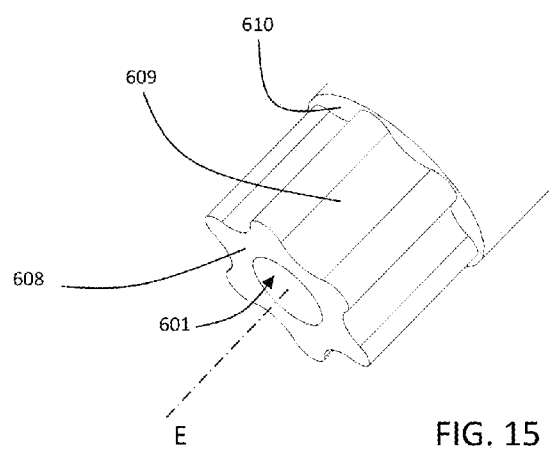
FIG. 15

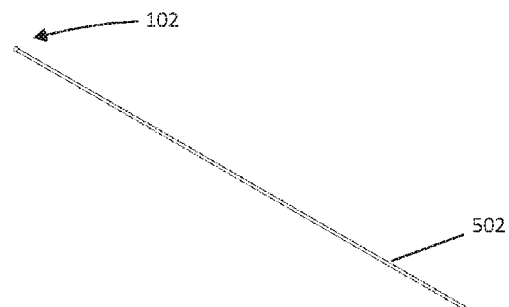
FIG. 21
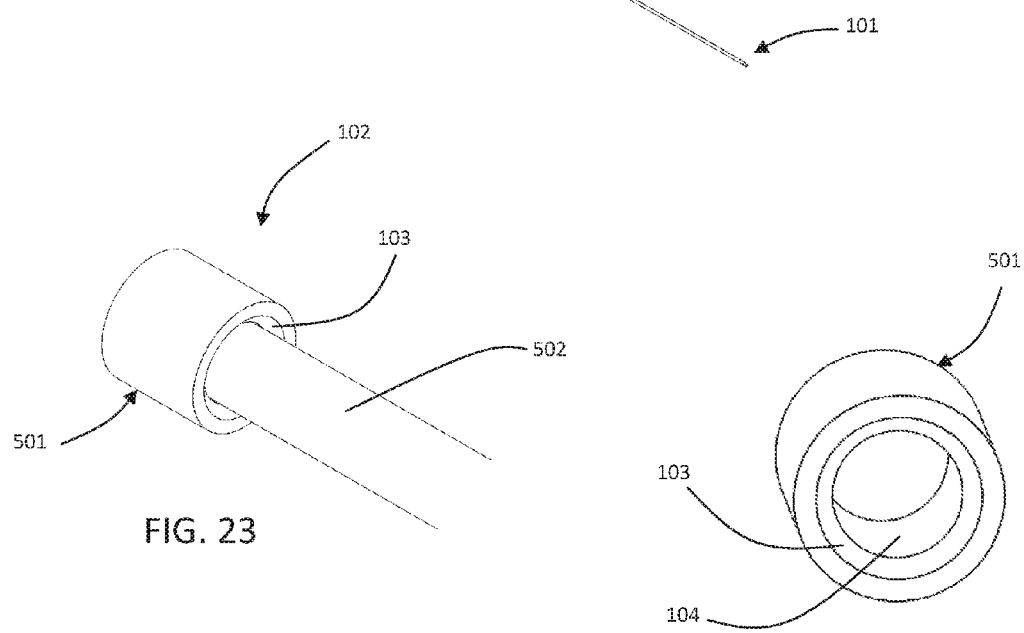
FIG. 23
FIG. 22
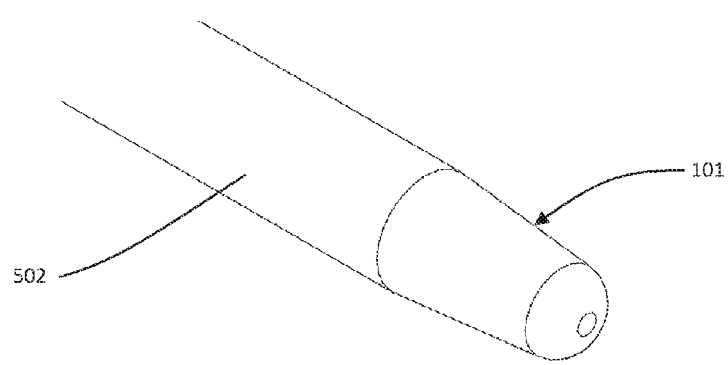
FIG. 24

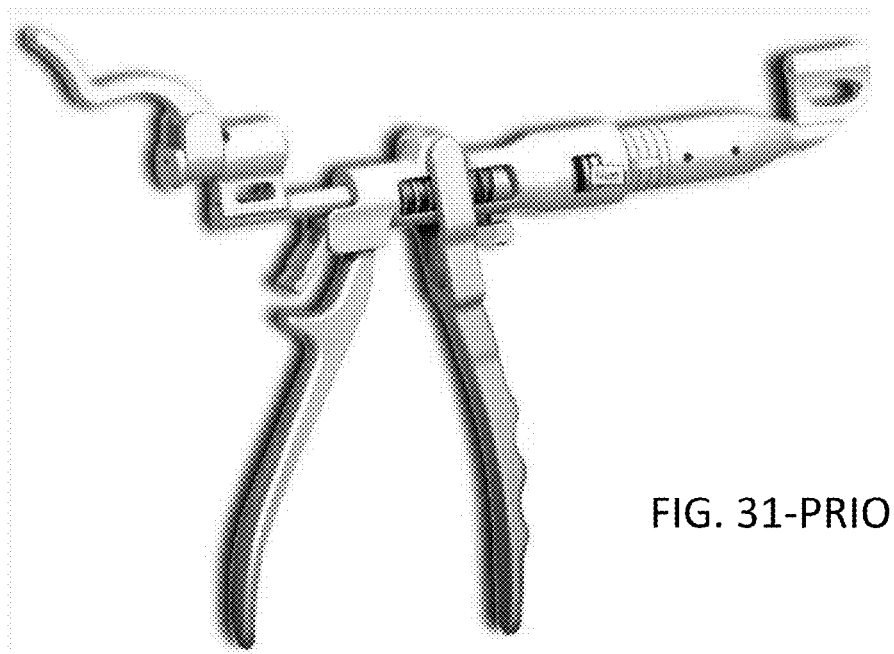
FIG. 31-PRIOR ART
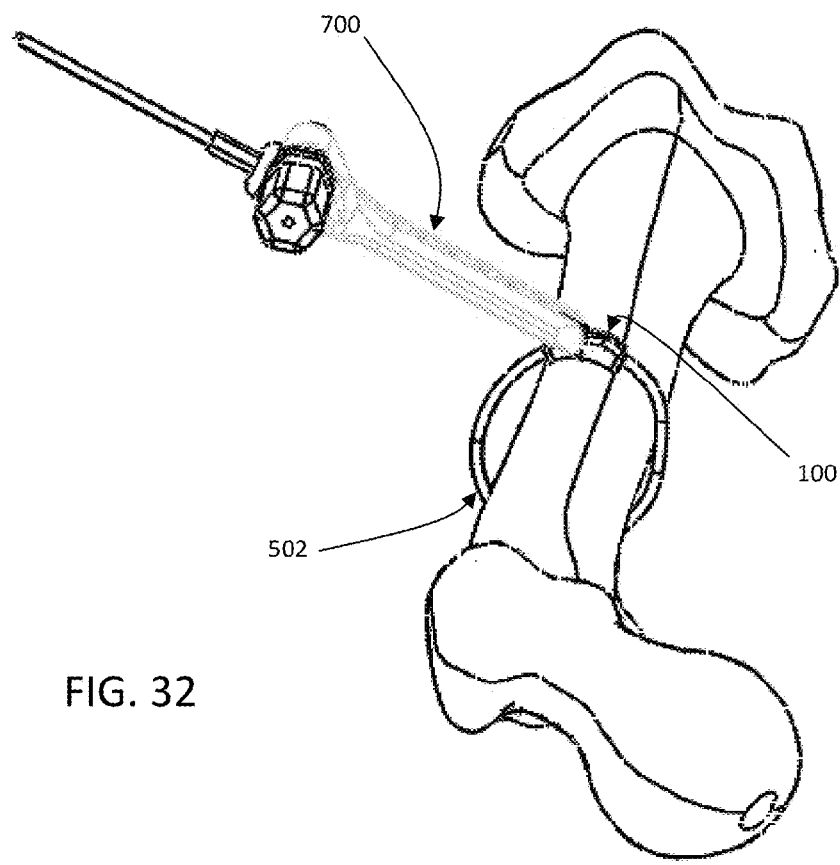
FIG. 32

CABLE FIXATION DEVICE

CROSS REFERENCE TO RELATED APPLICATIONS

This application claims priority to Provisional Patent Application No. 61/801,837 filed Mar. 15, 2013, the entire disclosure of which is hereby incorporated by reference and relied upon.

BACKGROUND OF THE INVENTION

1. Field of the Invention

The invention relates generally to implants and instruments utilized for the fixation of the skeleton, and more particularly to implants and instruments utilizing surgical cable.

2. Description of Related Art

Surgical wires and cable has a history of use for the repair of the skeletal system. Their usefulness has suffered due to various deficiencies in their function.

For example, Kilpela et al. in U.S. Pat. No. 5,415,658 discloses a cable loop connector. When utilizing this connector, the instruments required to tension the cable and lock the cable are situated along two axis's more than 90 degrees apart. This excessively wide spread between instruments requires a larger incision and increases difficulty in handling. In addition, the locking portion of the connector utilizes an internal crimp making it unuseable for a plurality of locking and unlocking cycles when cable re-adjustments are needed.

Mattchen et al. in U.S. Pat. No. 7,207,090 discloses another form of cable retaining device for retaining flexible cables under tension. The device includes a body with an internal tapered void. A wedge shaped plug with recessed edges for containment of a cable is slidable into the void therein locking the cable between the body and plug. During clamping the slidable plug creates friction against the cable member potentially damaging the cable. Due to this, this system is also unsuitable for a plurality of locking and unlocking cycles.

Allen et al. discloses in U.S. Pat. No. 7,255,701 various forms of looped cable locking mechanisms. Most embodiments suffer from having each end of the cable loop spaced from each other along the long axis of the bone under repair. The cable within the loop fails to lay in the same plane therein causing a torsional force on the locking mechanism and improper seating on the bone. In addition, the disclosed embodiments have a tensioning axis that is not aligned with the locking axis causing difficulties using instrumentation within a small surgical access space.

Justin el al. discloses in U.S. Pat. No. 8,241,288 a collet fixation system for a cable loop and a cable locking instrument. In this bone fixation element, a cable passes through a pair of passageways in which the cable is secured. These passageways are separated by a space along the length of the bone therein once again imparting a torsional force on the fixation element as the cable is tensioned and causing it to not seat properly on the bone. An additional shortcoming is that the collet in this device is threaded. The collet will collapse down and bind the cable as the collet is advanced in rotation causing the cable to be twisted therein imparting unnecessary torsional forces on the cable that could lead to failure. An instrument is disclosed for advancing the collet while stabilizing the fixation element from rotation. Integrated within the C-shaped frame of the instrument is a handle of a collet driver co-aligned with the longitudinal axis of the collet. The positioning of the handle within the frame makes the drive handle both difficult to reach by hand and difficult to impart a hand torsional force. Also, the instrument utilizes a plurality of prongs (6) spaced in a radial pattern to interface with the fixation element. The quantity of prongs and their rounded profile is not well suited for firm control over the fixation element.

Several other cabling systems utilize crimps to lock the cable loop in a predetermined cable tension. These systems generally cannot be repeatedly "unlocked" then "relocked" when further adjustments by the surgeon need to be made.

BRIEF SUMMARY OF THE INVENTION

Disclosed herein is a cable fixation device useful for repairing the skeletal system while overcoming the short comings identified in the surgical cable implant and instrument prior art. The system utilizes a clamp housing that fixes a butt end of a surgical cable within a drum channel located in the clamp housing. In the operative configuration the cable is looped around the bone segment and reentered through a lock aperture in the clamp housing then through a collet and lock cap residing within the lock aperture. The cable loop and each of these forementioned components comprise a central axis situated within a single plane therein preventing any torsion forces on the clamp body that may cause it to cant on the bone. A sliding interface is situated between the lock cap and collet wherein advancing the lock cap does not impart rotation on the collet and twisting of the surgical cable that could otherwise lead to cable failure. In addition, the collet locking mechanism is non-abrasive and otherwise non-destructive to the cable providing the capability to repeatedly unlock and relock the cable without damage to the cable. The axis for tensioning of the cable is generally coincident with the axis on which the lock cap is advanced for locking. This feature simplifies the surgical procedure by eliminating the need for use of a cable tensioner on one axis and the use of a cap locking instrument on a different axis. This reduces the size of incision required to operate the instrumentation therein enabling the surgery to be performed minimally invasively The cable fixation device is also configured for optional assembly during surgery in preferred embodiments. With this feature the cable may be passed in either direction through the cable passer. A specialized counter torque instrument is disclosed having a torsional input shaft at a position 90 degrees to the elongated axis of the instrument. This arrangement offers a tremendous ergonomic improvement to the surgeon attempting lock the cable construct within a surgical site.

BRIEF DESCRIPTION OF THE SEVERAL VIEWS OF THE DRAWINGS

These and other features and advantages of the present invention will become more readily appreciated when considered in connection with the following detailed description and appended drawings, wherein:

FIG. 8 is a top perspective view of a cable collet;

FIG. 9 is a side perspective view of a cable collet illustrated in FIG. 8;

FIG. 10 is a bottom perspective view of a cable collet illustrated in FIG. 8;

FIG. 13 is a side perspective view of a cannulated driver.

FIG. 14 is a side perspective exploded view of a cannulated driver illustrated in FIG. 13.

FIG. 15 is a close up view of the drive faces of a cannulated driver illustrated in FIG. 13.

FIG. 21 is a side perspective view of a surgical cable assembly.

FIG. 22 is a perspective view of a cable drum.

FIG. 23 is a close-up perspective view of the butt of the cable and cable drum illustrated in FIG. 21.

FIG. 24 is a close-up perspective view of the lead of the cable illustrated in FIG. 21.

FIG. 25A is an upper surface view of a preferred embodiment a cable fixation device in a looped configuration.

FIG. 31 is a perspective view of one form of a cable tensioner found in the prior art for tensioning surgical cable prior to locking the implant construct.

FIG. 32 is a perspective view of a human femur bone with a cable fixation device in a looped configuration encircling a damaged bone with an attached counter torque locker.

DETAILED DESCRIPTION OF THE INVENTION

Referring to the figures, wherein like numerals indicates like or corresponding parts throughout the several views, numerals of different embodiments are separated by 1000. Similarly, corresponding axes of different embodiments are indicated with a repeated letter.

Figure 1:
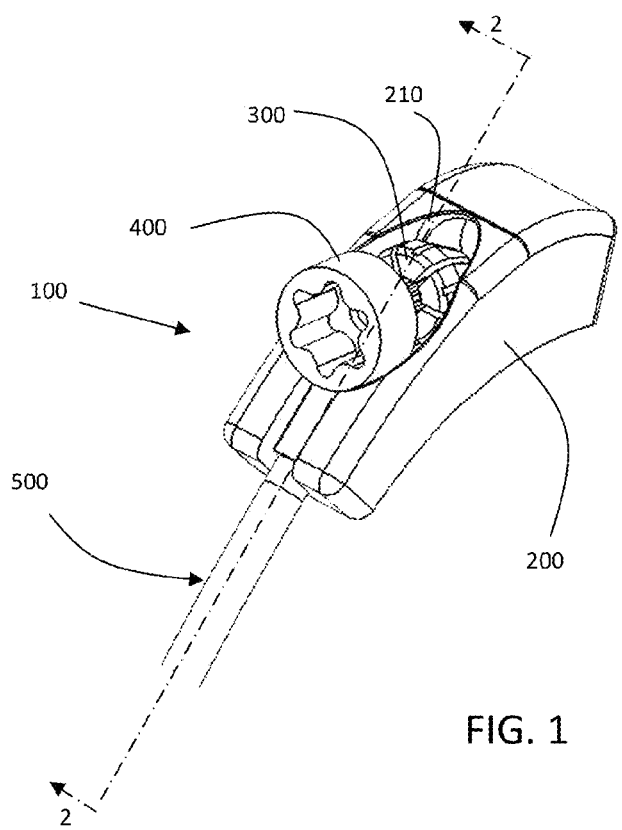
FIG. 1 is top perspective view of a cable fixation device illustrating only a portion of the cable that will be utilized in the construct.

An embodiment of a cable fixation device 100 is illustrated in FIG. 1. The device comprises a clamp housing 200, a cable collet 300, a lock cap 400, and a cerclage cable assembly 500.

Figure 25:
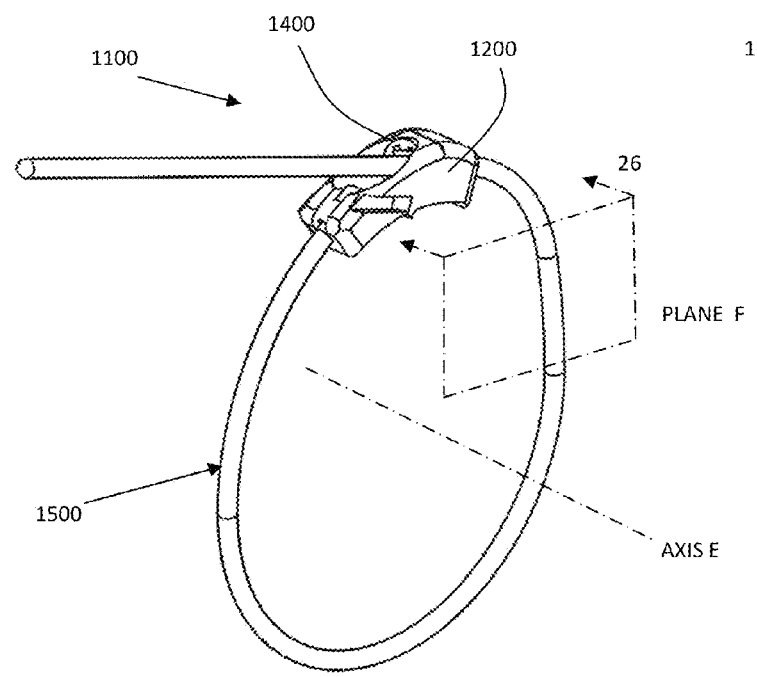
FIG. 25 is a perspective view of a preferred embodiment of cable fixation device in a looped configuration.
Figure 25:
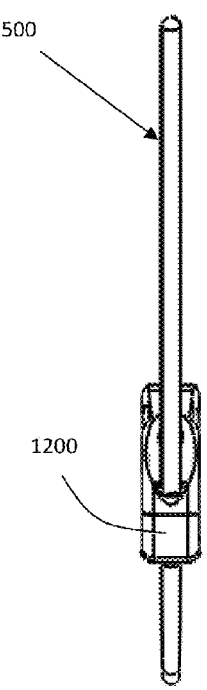

As illustrated in FIG. 32, the cable fixation device 100 is useful during surgery to secure segments of bone together by encircling the cerclage cable assembly 500 around the bone then tensioning and securing the cable. The long axis of the bone is situated generally coaxial with axis E of the loop as illustrated in FIG. 25.

Figure 2:
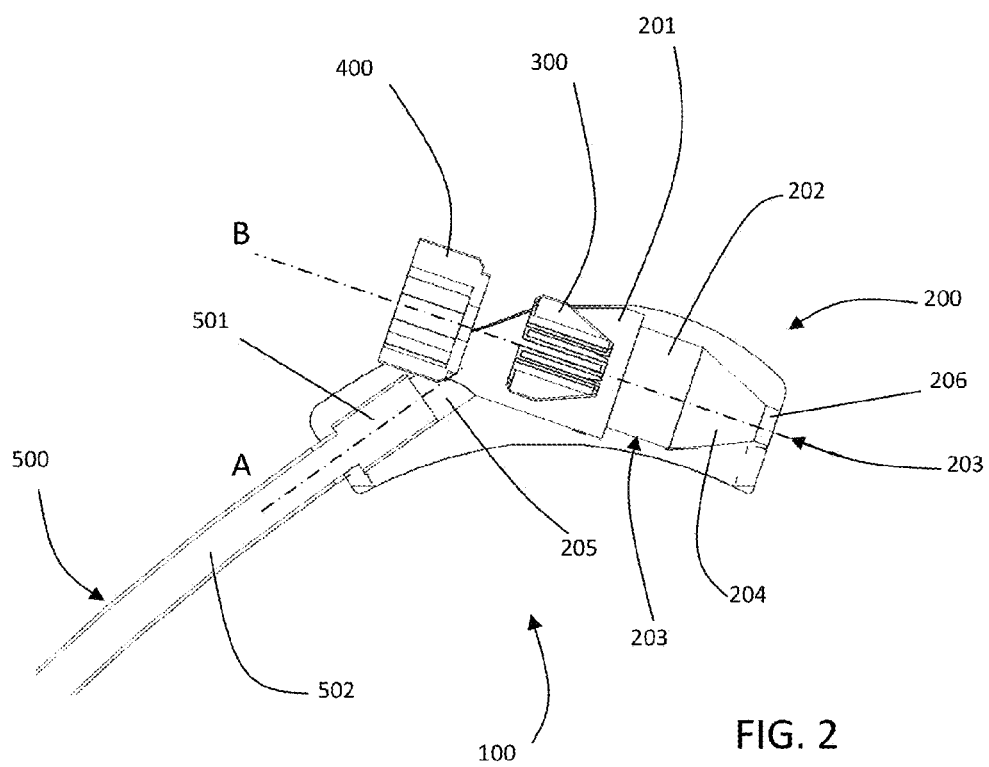
FIG. 2 is cross-sectional view of the cable fixation device illustrated in claim 1 again showing only a portion of the cable.

In one embodiment, cerclage cable assembly 500 (FIGS. 1 and 2) comprises a cable 502 (FIG. 21), a butt 102, a cable drum 501 (FIGS. 22 and 23), and a cable lead generally indicated at 101 (FIG. 24). The word 'cable' used herein may refer to many different elongate tensioning forms. For example, in alternative embodiments cable 502 may be in the form of a wire or line. Each component of the cable fixation device and instruments is made of biocompatible materials typically titanium or stainless steel alloys although polymers such as PEEK may be utilized as well. Cable 502 in preferred embodiments is approximately 1.8 mm in diameter and woven from a blend of titanium or titanium alloy strands for a predetermined blend of flexibility and strength. Cable lead 101 is preferably tapered and formed with a smooth surface to keep all cable strands tightly wound for eased entry into cable apertures or channels of housing 200 and through instruments and to prevent injury to the patient or surgeon. For example, lead 101 may be swaged.

The butt 102 opposes lead 101 (FIG. 21) on cable 502 and comprises the cable end configured for anchoring within clamp housing 200. In preferred embodiments the butt 102 (FIG. 23) comprises an enlarged terminal portion illustrated here in the form of a cable drum 501 pressed on the cable. The drum 501 comprises a cylindrical sleeve with one or more entry faces 103 that are tapered or radiused. The clamp wall 104 diameter of drum 501 is sized to impart sufficient friction at the cable surface to prevent being pulled off due to tensioning of cable 502 or due to other forces imparted by the patient's skeletal system. Other methods may be used to secure drum 501 on cable 502 and may include for example welding, crimping, or molding. In alternate embodiments the butt may take other forms such as simply the cut end of the cable wherein a portion of the clamp housing is crimped on the cable.

Each component of the cable fixation device 100 partially resides within clamp housing 200. As seen in FIGS. 3-7, the housing 200 comprises a block body generally indicated at 218. Formed on body 218 is a pair of opposing side surfaces 208, a front end or leading surface 209, a rear end surface or trailing surface 211, an upper surface 207, and a bottom surface 216.

Figure 4:
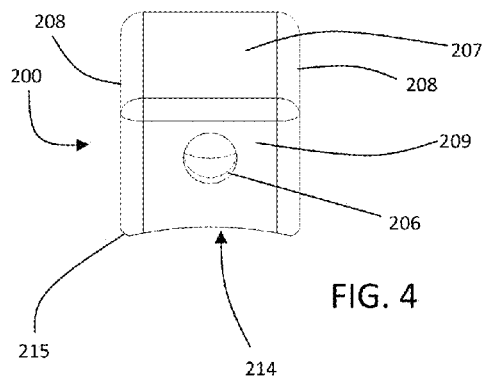
FIG. 4 is an end view of the clamp housing illustrated in FIG. 3.
Figure 3:
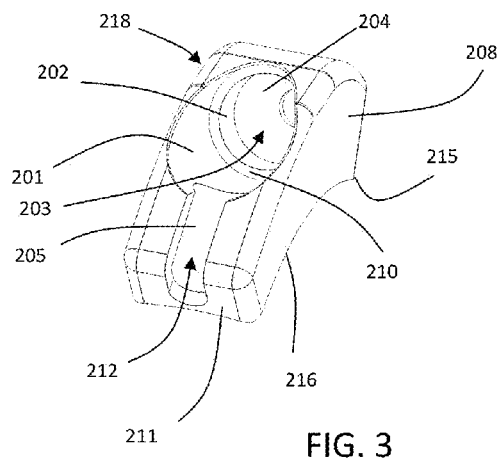
FIG. 3 is a top perspective view of a clamp housing.
Figure 5:
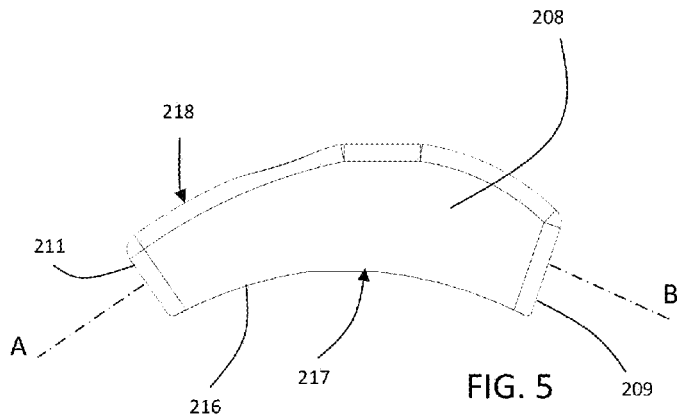
FIG. 5 is a side view of a clamp housing illustrated in FIG. 3.
Figure 6:
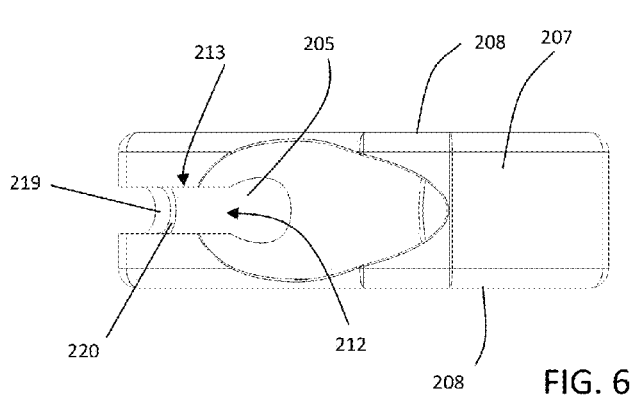
FIG. 6 is top view of a clamp housing illustrated in FIG. 3.
Figure 7:
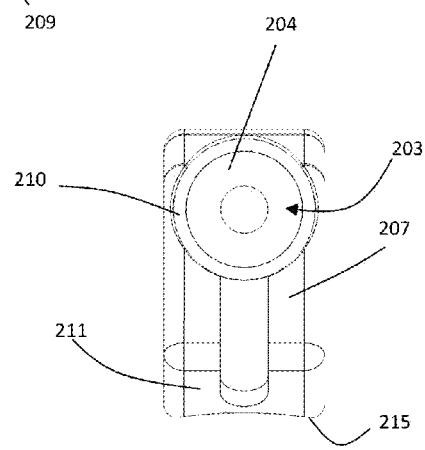
FIG. 7 is an opposing end view of a clamp housing illustrated in FIG. 3.

To assist in proper fit of housing 200 on the bone surface, the bottom surface 216 is concave as generally indicated at 217 of FIG. 5. In this embodiment, the radius of the concave is less than the radius of the bone surface onto which it will be seated. Further in this embodiment, bottom surface 216 is concave between opposing side surfaces 208 as generally indicated at 214 of FIG. 4.

Together, the concave surface at 217 and 214 define feet 215 at each corner of bottom surface 216 of body 218. These feet 215 may be sharpened or extended into the form of teeth in some embodiments and may penetrate the bone surface to prevent slippage of the clamp housing 200 across the outer surface of the bone when cable fixation device is in an operative configuration wherein cable 502 is secured in a loop around the bone segments with cable tensioned and secured to a pre-determined tension utilizing lock cap 400 advanced on cable collet 300.

Extending into the trailing surface 211 of body 218 along axis 'A' is a drum channel generally shown at 212. Drum channel 212 defines drum wall 205. Drum channel 212 is shaped and sized to house cable drum 501 (FIG. 2, 22) of cerclage cable assembly 500. Cable shelf 219 with drum stop surface 220 (FIG. 6) contain drum 501 in drum channel 212 preventing it from being pulled out of housing 200 when the cable 502 is tensioned. Cable slot generally indicated at 213 provides for the loading of cable 502 into drum channel 212 then provides for seating of the cable drum 501 into the drum channel 212 upon pulling of the free end of cable 502. In alternative embodiments, the butt 102 of cable 502 is secured in housing 200 by way of methods described earlier.

Figure 11:
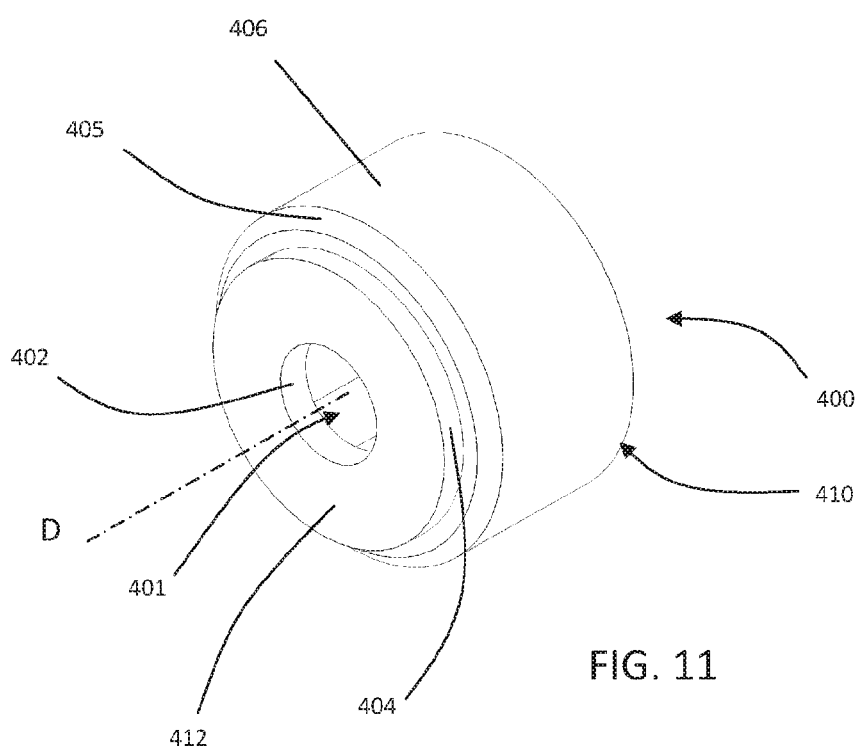
FIG. 11 is a bottom perspective view of a lock cap.

A lock aperture generally shown at 203 (FIGS. 2 & 3) is defined by a series of walls with various diameters. Passage wall 201 is sized in diameter to freely pass cable 502, the cable collet 300, and the lock cap 400. Step 210 transitions between passage wall 201 and fixation wall 202. Fixation wall 202 comprises features to fix the lock cap 400 in place. In this embodiment these fixation features are in the form of threads (not shown) formed in the surface of fixation wall 202 for co-engagement with threads (not shown) formed in fixation face 406 of lock cap 400 (FIG. 11). Alternatively, other co-engagement configurations may be utilized for fixation between the lock cap and clamp housing such as for example a bayonet connection.

Compression wall 204 (FIG. 2, 3,7) is tapered and complements lock wall 305 (FIG. 8-9) of cable collet 300 wherein when lock cap 400 is advanced along axis B, lock wall 305 is also driven causing collet 300 to compress and clamp on cable 502 thereby fixing cable in place. Inlet wall 206 (FIG. 4) is sized sufficiently large to freely pass cable 502 while small enough to prevent passage of collet 300. In alternative embodiments, compression wall 204 may assume other forms such as a smaller diameter step to serve a similar function of compressing collet.

Cable collet 300 is illustrated in FIGS. 8-10. In this embodiment, the collet 300 comprises a curved body 311 with clamp surface 301 extending therethrough along axis 'C'. Clamp surface 301 defines central aperture 306 sized sufficient in diameter to pass cable 502. Formed in curved body 311 is a bottom face 307, a top face 303, a lock wall 305, and a head face 302. The curved body 311 may comprise one or more tapered face 304. Extending from the top face 303 are a plurality of top compression gaps 309 and extending from the bottom face 307 are bottom compression gaps 308. These gaps 308 and 309 are defined by gap walls 310. In this embodiment the gaps are cut linear along axis C and the gaps 308 radially alternate with gaps 309. In alternate embodiments these gaps may take other forms such as a spiral. At the bottom of each gap is a resilient wall 312 which flexes therein providing for central aperture 306 to reduce in diameter for cable clamping. In alternative embodiments collet 300 may be spherical.

Figure 12:
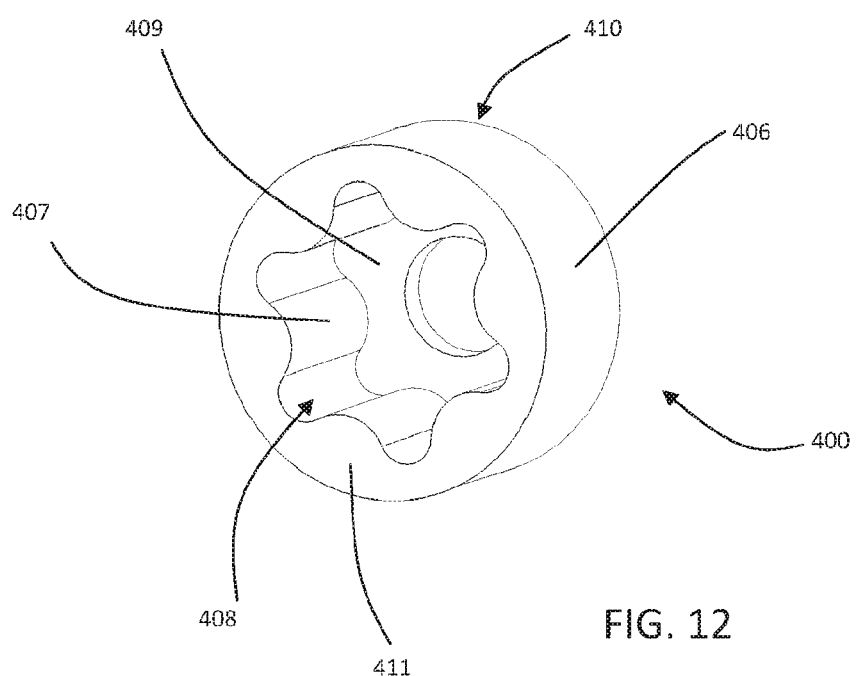
FIG. 12 is a top perspective view of a lock cap illustrated in FIG. 11.

Lock cap 400 (FIG. 11-12) comprises a cylindrical body 410 with central aperture 401 extending along axis D. Drive surfaces 407 define drive pocket 408 which extend into cylindrical body 410 from top surface 411. Drive pocket 408 is configured in shape to receive cannulated driver tip 602 (FIG. 15). At the bottom of drive pocket 408 is pocket base 409. Cable wall 402 defines central aperture 401. Aperture 401 has sufficient diameter to pass cable 502 through drive wall 412. Fixation face 406 engages fixation wall 202 of clamp housing 200 for locking. In this embodiment, fixation face 406 is threaded as is wall 202 (threads not shown). Threads on face 406 may include a lead in taper 405 to ease starting of threads. Step 404 decreases diameter of drive wall 412 to prevent interference with threads during assembly.

Figure 19:
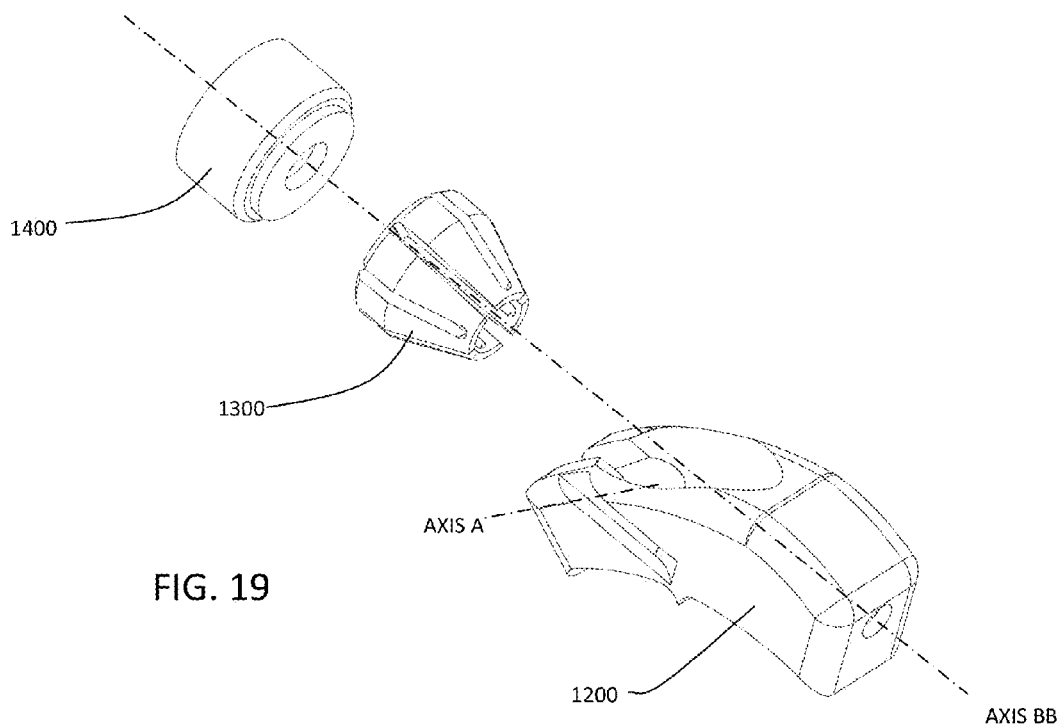
FIG. 19 is an exploded view of a preferred embodiment of a clamp housing, collet, and lock cap.
Figure 26:
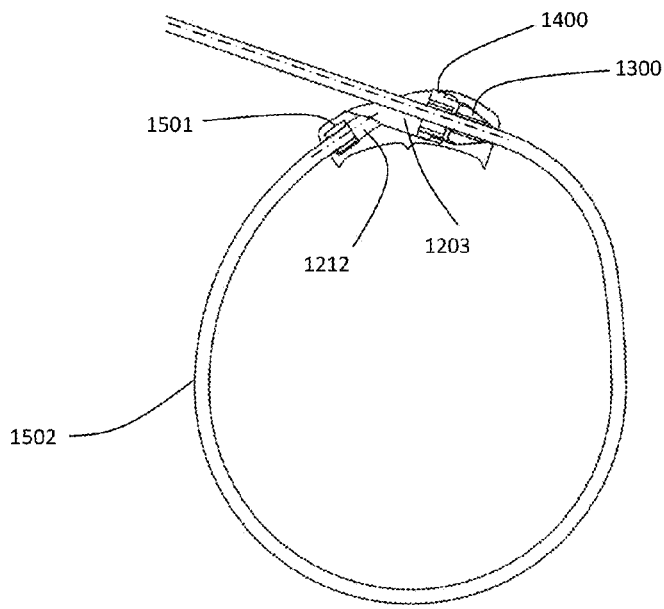
FIG. 26 is a cross sectional view through plane F of a preferred embodiment of the cable fixation device in a looped configuration.

In preferred embodiments, drive wall 412 drives with sliding engagement against top face 303 of collet 300 during locking. Due to this sliding engagement, a rotation of the lock cap 400 does not cause rotation of the collet 300 and therefore cannot induce rotation between clamp surface 1301 and cable 1502. In addition, the sliding engagement between lock cap 400 and collet 300 provides for pushing of the collet 300 linearly along axis C such that clamp surface 301 slides along the cable until the collet collapses down therein locking cable 1502 in place. In the preferred embodiments illustrated in FIGS. 8, 9, and 11, top face 303 and drive wall 412 are orientated generally perpendicular to the central apertures 306, 401 which extend through the collet 300 and lock cap 400. As illustrated in FIGS. 19 and 26, the long axis of the cable passes through these central apertures along Axis BB. Therefore, in these embodiments the sliding engagement between top face 303 and drive wall 412 occurs in a plane generally perpendicular to the long axis of the cable.

As an alternative, lock cap 400 and collet 300 may be unitary wherein rotation of lock cap 400 will cause 1:1 rotation of the collet 300. This approach is less preferred and is noted in the prior art. Here, the clamp surfaces within the collet induce a twist on the cable 502 as the collet 300 tightens around it that can lead to abrasion and fraying of the cable. In addition, the cable surface has inherent irregularities which become bound in the collet prematurely therein causing the cable to be pushed distally during locking and leading to an undesired reduction in cable cerclage tension.

FIGS. 13-15 illustrate cannulated driver 600. This instrument is used to advance lock cap 400. The driver 600 comprises a drive shaft 603 with central cable aperture 601 extending the length of the instrument for passage of cable 502. At the distal end of drive shaft 603 is driver tip 602 with drive faces 609 configured to be received in drive pocket 408. Drive faces 609 will transmit torsional forces applied by the user at the handle 605 into drive surfaces 407 in the lock cap for advancement toward collet 300 for locking or away from collet for unlocking. Distal stop surface 608 and proximal stop surface 610 are advanced in to drive pocket 408 until seated against top surface 411 or pocket base 409. Drive shaft 603 may be configured as a singular shaft extending through handle 605 or as illustrated may be configured in segments to include proximal shaft 612. In this configuration, each shaft comprises fixation bosses 604 and 606 to seat within and assemble within handle 605. One or more fixation holes 613 may house pins or screws holding handle to drive shaft 603. Located at the proximal end of proximal shaft 612 is tensioner face 611 for interfacing with a tensioner instrument.

Figure 16:
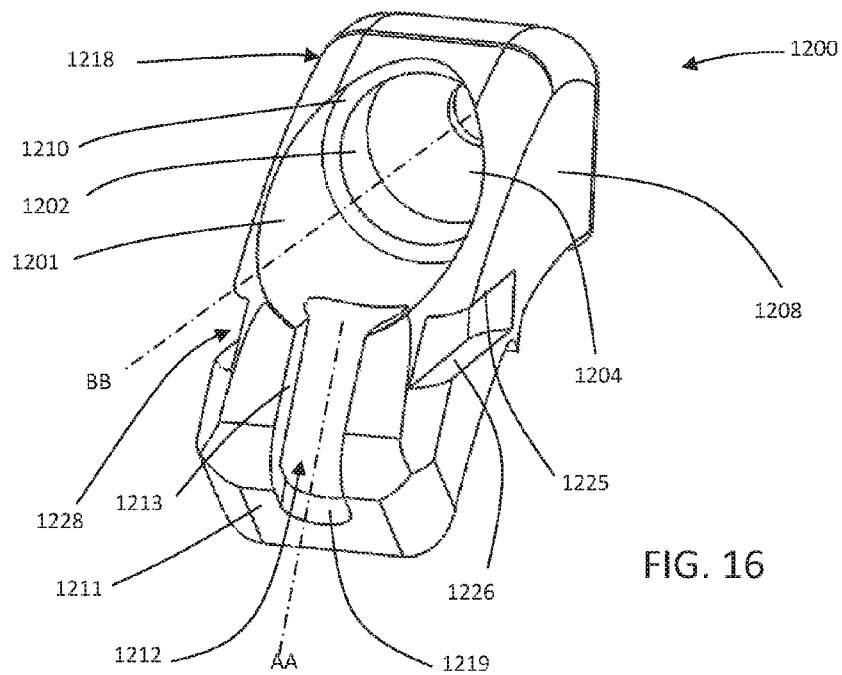
FIG. 16 is a top perspective view of a preferred embodiment of a clamp housing.
Figure 17:
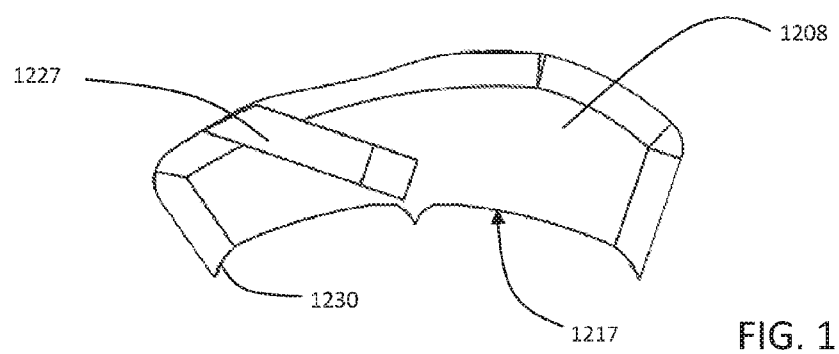
FIG. 17 is a side view of a preferred embodiment of a clamp housing illustrated in FIG. 16.
Figure 18:
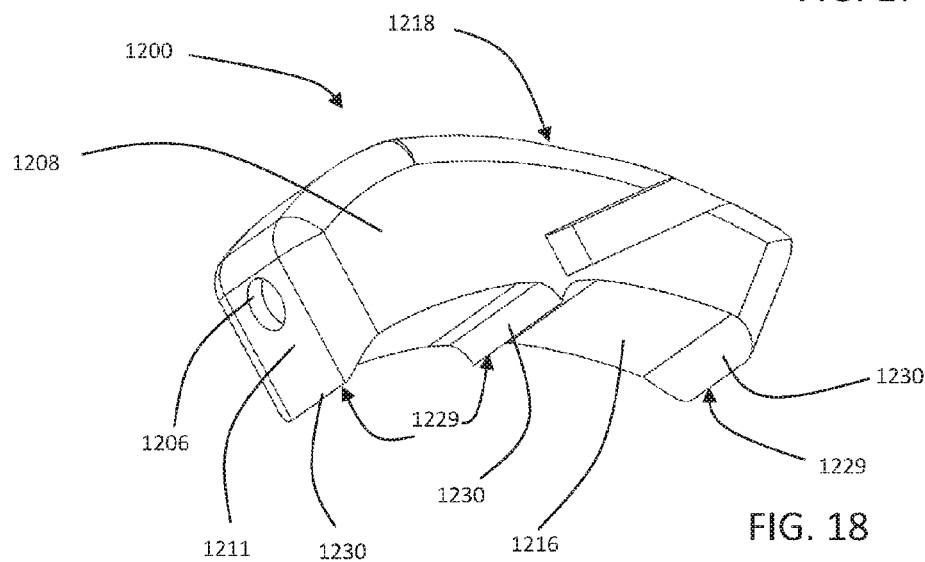
FIG. 18 is a bottom perspective view of a preferred embodiment of a clamp housing illustrated in FIG. 16.

FIGS. 16-18 illustrates a preferred alternative clamp housing 1200 comprising many of the same features of clamp housing 200. Again, corresponding parts are offset by 1000. For example, opposing side surfaces 208 on clamp housing 200 are identified as opposing side surfaces 1208 on the clamp housing 1200.

Figures 27, 27A, 27B:
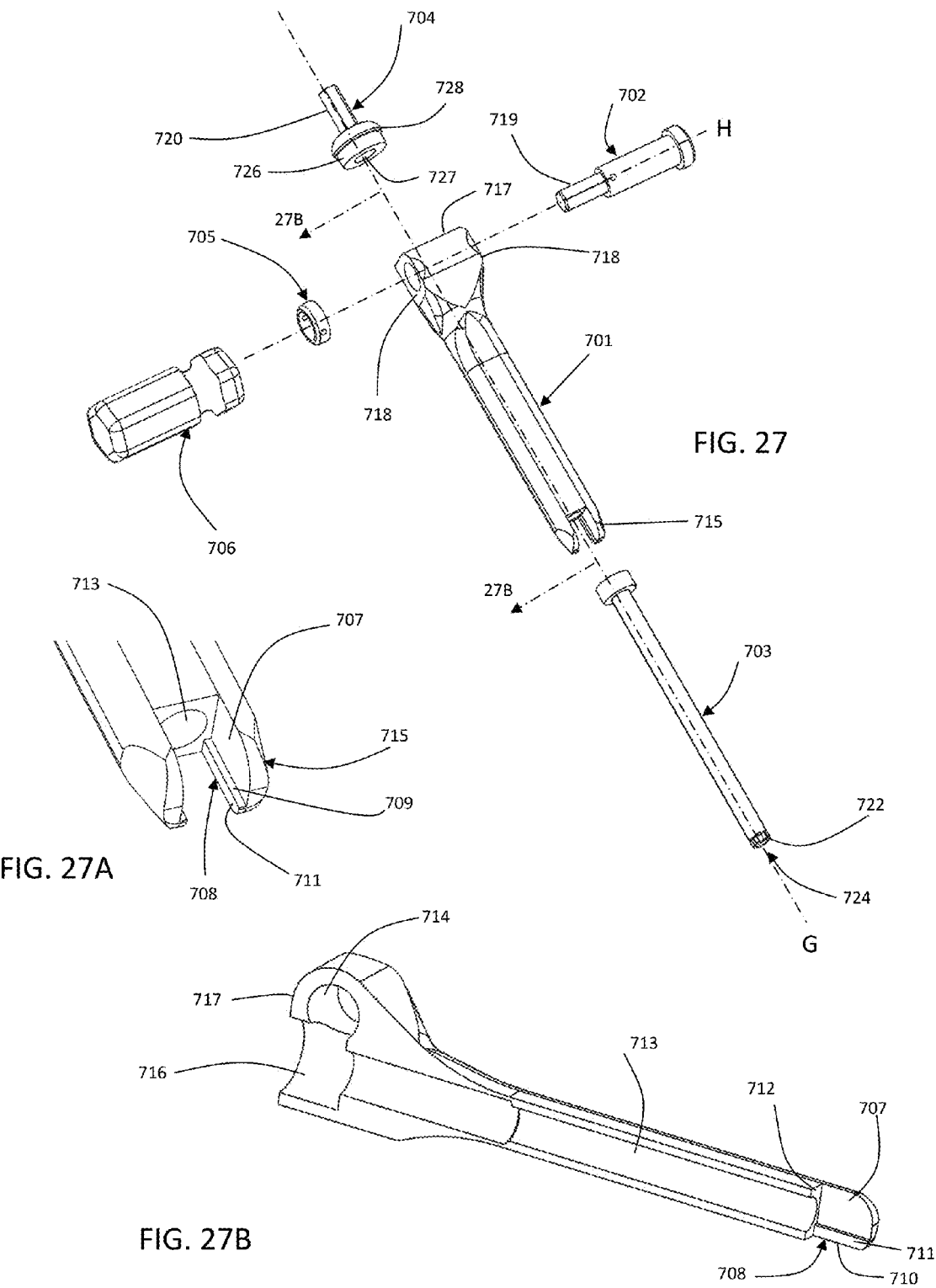
FIG. 27 is an exploded perspective view of a preferred embodiment of a counter torque locker instrument.
FIG. 27A is a close-up perspective view of control arms of the counter torque locker illustrated in FIG. 27.
FIG. 27B is a cross-sectional view of the clamp base illustrated in FIG. 27.

Extending into each opposing side surface 1208 is a pair of opposed control slots 1228 traveling parallel yet offset from axis BB. Control slots 1228 house control tabs 708 extending from clamp base 701 (FIG. 27). Control slots 1228 are bounded by opposed upper tilt wall 1225 and lower tilt wall 1226 and medially by steering wall 1227. Projecting from bottom surface 1216 are a plurality of teeth 1229 illustrated here in the form of elongated sharps 1230 extending between opposing side surfaces 1208. The concave curvature shown at 1217 of bottom surface 1216 remains in this embodiment, however concave surface 214 illustrated in FIG. 4 is absent. The elongate sharps 1230 and bottom surface 1216 are generally linear between opposing side surfaces 1208 as illustrated in FIG. 18.

Figure 20:
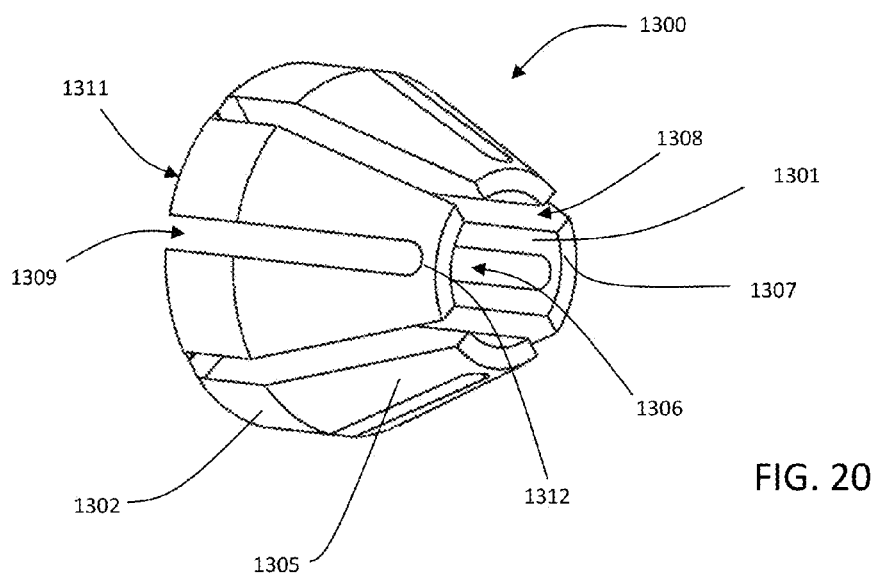
FIG. 20 is bottom perspective view of a preferred embodiment of a cable collet.

FIG. 20 illustrates an alternative collet 1300 having $\frac{1}{3}^{rd}$ less bottom compression gaps 1308 and top compression gaps 1309. In this embodiment, rather than terminating in a squared corner, each compression gap terminates in a rounded corner to improve flexibility and prevent stress concentrations. In some embodiments these rounded corners are formed by EDM machining.

FIG. 25 illustrates cable fixation device 1100 with cerclage cable assembly 1500 formed into a loop as if wrapped around bone segments. As in previous embodiments, the cerclage cable assembly 1500 resides in a single plane here shown as plane F and generally perpendicular to axis E. This single plane alignment is further illustrated in FIG. 25A and is responsible for the absence of torsional forces on the clamp housing 200 that may cause it to cant on the bone when cable 1502 is tensioned and locked in the operative configuration. On competing devices wherein the cable loop is not aligned in a single plane, the instrumentation utilized to hold the clamp housing during insertion to the surgical site and during tensioning and locking will counteract torsional forces on the clamp housing to keep the housing aligned. However, the clamp housing will cant on the bone causing a loss in cable tension as soon as the instrumentation is removed. This leads to a reduction in the stability provided by the cable and clamp construct. Illustrated in FIG. 26 is a cross section of cable fixation device 1100 through plane F also illustrating the internal components of the assembly having a co-planar elongate axis.

Figure 29:
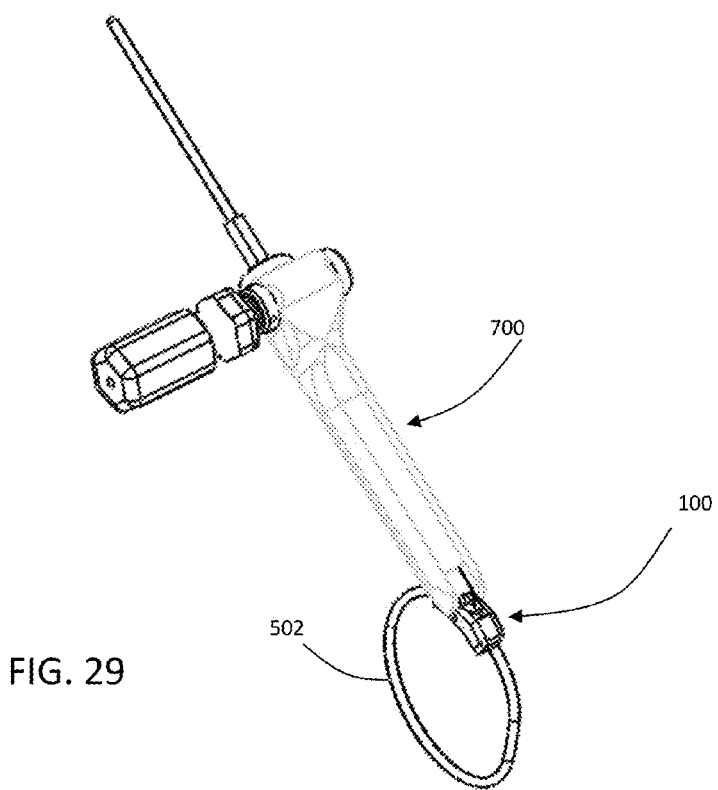
FIG. 29 is a perspective view of a counter-torque locker mated to a cable fixation device in a looped operative configuration.

As noted earlier, some embodiments of the clamp housing include control slots for attachment of a counter torque locker. A preferred embodiment of a counter torque locker 700 is illustrated in FIG. 29 with attached cerclage cable assembly 1500. FIG. 27 illustrates an exploded view of counter torque locker 700 for viewing of internal parts. Clamp base 701 serves to contain several parts of the assembly. Worm rod 702 is situated generally perpendicular within the proximal end of clamp base 701 and is generally co-axial with axis H. Worm shaft 703 is situated generally co-axial with axis G within clamp base 701. Hat 704 is situated within the proximal portion of clamp base 701 and is also generally co-axial with axis G. Worm retainer 705 is generally co-axial with axis H as is drive bar 706.

A cross sectional view of clamp base 701 is illustrated in FIG. 27B. Control arm 715 extends from base 701 at the distal end. Opposing containment walls 707 are spaced to house opposing side surfaces 208 of clamp housing 200 therebetween. Control tabs 708 extend parallel to axis G and are sized and positioned to fit in control slots 1228 of clamp housing 1200. The control tabs 708 comprise mating walls positioned to mirror with the upper tilt wall 1225, lower tilt wall 1226 and steering wall 1227 of clamp housing 1200. These mating walls are the upper mirror 709, lower mirror 710, and steering mirror 711. Proximal to control arms 715 is stop wall 712 situated to abut clamp housing 200 when the clamp base 701 is fully engaged with it and lock cap 1400 is fully advanced to locking.

Clamp base 701 comprises an internally positioned shaft guide 713 extending down the length of base 701 sized to house worm shaft 703 therein. Along axis H, worm guide 714 extends through a proximal portion of clamp base 701. At the proximal end of clamp base 701 resides hat seat 717 for seating hat 704 thereagainst. Inset the proximal end of clamp base 701 is hat guide 716 sized and shaped to house hat 704 therein.

Figure 28:
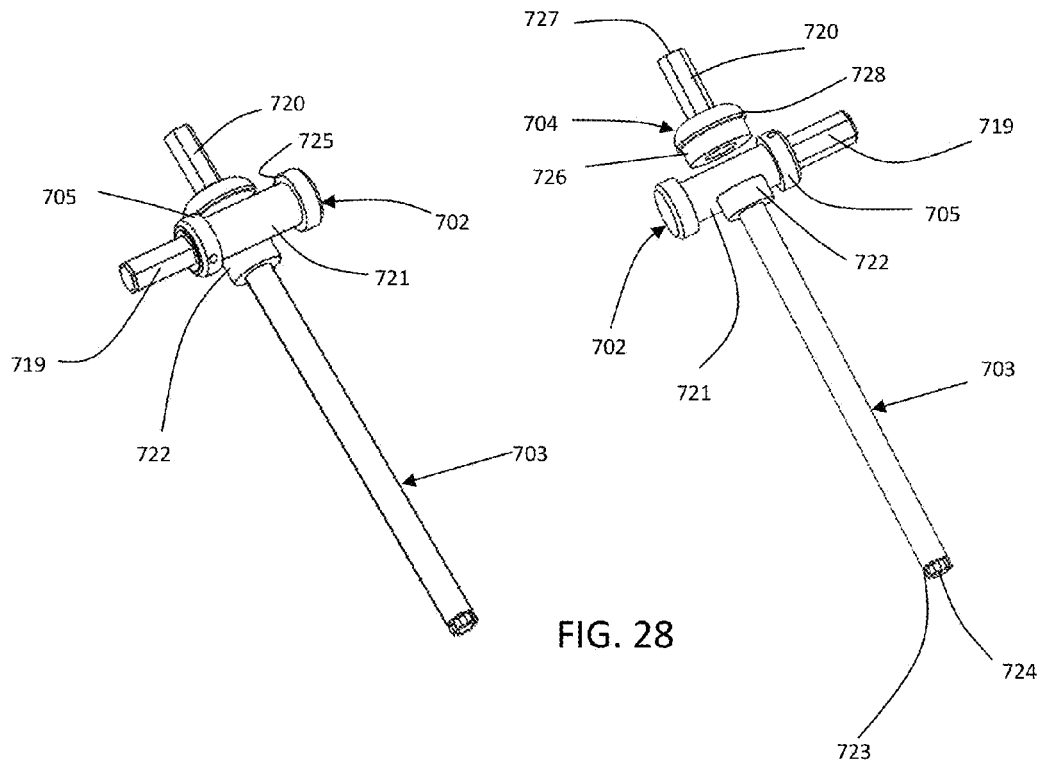
FIG. 28 illustrates two perspective views of the internal gear and shaft mechanisms of the counter torque locker illustrated in FIG. 27.

FIG. 28 illustrates the internal gear mechanisms. Worm rod 702 resides within worm guide 714 and rotates freely therein. Worm shaft 703 resides within shaft guide 713 and also rotates freely therein. The worm rod 702 comprises a worm helix 721 (shown in location only) on its outer surface for functioning as a worm drive. The worm rod 702 comprises a worm shoulder 725 for securing the worm drive against one of the worm walls 718. A worm retainer 705 is removably positioned on worm rod 702 opposite the worm shoulder 725 to secure the worm rod 702 in a predetermined position within clamp base 701. Interior to worm shaft 703 is cannula 724 which extends the entire length along axis G and is sized to pass cable 502. At the distal end of worm shaft 703 is drive boss 723 with complementing surfaces for residing within drive pocket 1408 and transmitting torsional forces to drive surfaces 407 to advance lock cap 400. Alternatively, worm shaft 703 may be configured with a drive bit detachable from worm shaft 703 such that the drive bit is replaceable as it wears. In one form this drive bit will be backed by a spring biasing the drive bit distally such that as lock cap 1400 is advanced distally the drive bit will stay entirely engaged in the drive pocket 408. At the proximal end of worm shaft 703 are radially placed worm teeth 722 (shown in location only) shaped to inter-digitate or otherwise mesh with the worm helix 721 formed on worm rod 702 to provide a worm and worm gear relationship.

Hat 704 comprises a hat base 726 sized for secure fit within hat guide 716 of clamp base 701 and positioned by hat lip 728 abutting hat seat 717. Hat tunnel 727 extends through hat 704 along axis G and is sized for passing cable 502 therethrough. Hat pod 720 provides a proximal surface against which a distal end of a cable tensioning instrument (FIG. 31) may be placed.

Drive bar 706 comprises internal drive surfaces (not shown) for acting on complementing worm drive 719 surfaces of worm rod 702. Torsional forces imparted by the user on drive bar 706 causes rotation of the worm rod 702. These forces are imparted through the worm helix 721 to worm teeth 722 therein causing the drive boss 723 to advance lock cap 1400 in a direction that will cause either tightening or loosening of collet 1300 around cable 1502.

The instruments disclosed for tensioning cable 1502 and advancing lock cap 1400 are generally co-aligned along axis B during operation. This feature simplifies the surgical procedure by eliminating the need for handling of a cable tensioner positioned on one axis and the use of a cap locking instrument on a different axis. This co-alignment also provides a minimally invasive approach for completing the surgery as it reduces the size of incision required to operate the instrumentation. In addition, the cable fixation device 100 disclosed herein utilizing the collet 300 and lock cap 400 fixes the cable 502 at the tension applied by the tensioner without loss of tension.

The cable fixation device 100 will preferably be packaged pre-assembled with collet 300 loosely seated within compression walls 204 and lock cap 400 loosely threaded within fixation wall 202. The cable drum 501 is pre-seated within drum walls 205. A surgical kit may be provided for use in the surgical suite comprising the cable fixation device, the cannulated driver, the counter torque locker, a cable passer, and a cable tensioner.

Figure 30:
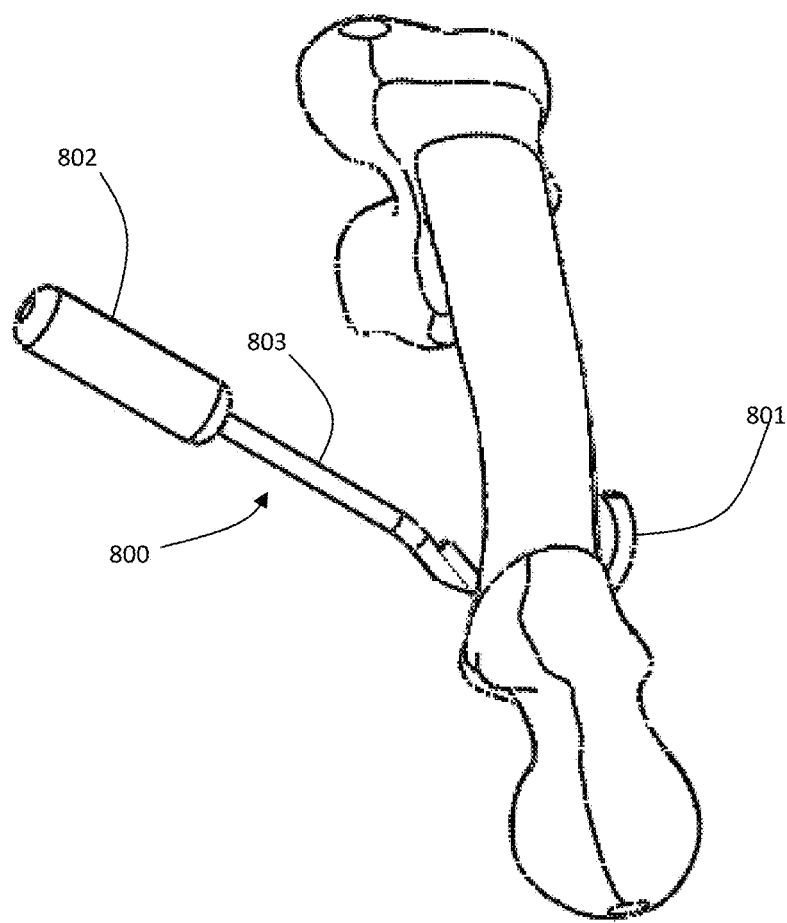
FIG. 30 is a perspective view of a human femur with a cable passer in position to loop a cable around the bone from a surgical incision site.

The cable fixation device 100 is utilized by passing the free end of the cable around the bone or bone segments to be stabilized. A cable passer 800 (FIG. 30) may be utilized for this purpose. The passer typically comprises a passer handle 802 connected to a passer shaft 803 for guiding a semi-circular passer tube 801 around the outer surface of the bone. The surgical cable is fed into the passer tube 801 until exposed out the other side. The passer 800 may then be removed leaving the cable 1502 encircled around the bone. The lead 1101 of cable 1502 is then fed through inlet wall 1206 of clamp housing 1200, through the central aperture 1306 of the collet 1300, and through the cable wall 1402 of lock cap 1400. In an optional provisional locking step, the surgeon may choose to use cannulated driver 600 (FIG. 13) to temporarily secure the cable. In this event, the cable lead 1100 is fed through central cable aperture 601 of driver tip 602 until the lead 1101 exits tensioner face 611. The driver tip 602 is then seated in drive pocket 1408. Grasping the cable lead, the surgeon snugs the cable to a desired cable tension then applies hand torque on handle 605 to advance lock 1400 until cable collet 1300 compresses around cable 1502 to secure the loop. The surgeon may choose to move on to secure other cables before returning to perform final locking. In preferred methods, driver 600 is then removed and replaced with counter torque locker 700. The cable lead 1100 is fed though cannula 724 of worm shaft 703 until lead 1101 exits hat tunnel 727. Drive boss 723 of counter torque locker 700 is seated in drive pocket 1408 and control tabs 708 are seated within control slots 1228 of clamp housing 1200. The lead 1101 of the cable 1502 is then fed into a standard surgical cable tensioner (FIG. 31). The counter torque locker 700 is used to loosen lock cap 1400 and the cable is tensioned to a predetermined tension therein causing the cerclage loop around the bone to tighten and elongated sharps 1230 to engage the bone surface. The surgeon then applies torque to drive bar 706 therein causing rotation of worm rod 702, worm shaft 703, and final advancement of lock cap 1400 therein forcing collet 1300 to collapse about cable 1502 securing the cable fixation device 100 at a predetermined cable tension. If the surgeon chooses, drive bar 706 or handle 605 may be derotated to loosen and remove the cable fixation device 100, 1100 or to retension to an alternative tension level before relocking without damage to cable 502, 1502. The tensioner and counter torque locker 700 may then be removed and excess cable lead trimmed.

In an alternative method, portions of the cable fixation device 100 may be assembled during surgery. In preferred embodiments the butt of the cable is configured in size to be passable through the cable passer then assembled with the clamp housing 200 after the passer instrument is removed. This feature provides for the cable 1502 to be passed in either direction through passer tube 801. In cases where introducing the passer instrument from one side of the bone is easier than the other, the surgeon may be forced with prior art systems to introduce the passer from the more difficult side to assure the clamp housing 200 is positioned in a convenient direction for tensioning and locking. This assembled in surgery feature ensures the surgeon will be able to enjoy the convenience of introducing the passer instrument around the bone from either entry position while also being assured the clamp housing will be directed in a convenient direction for tensioning and locking. Assembly in preferred embodiments is completed by passing the cable around the bone then dropping cable 1502 through cable slot 1213. Cable 1502 is pulled until cable drum 1501 is seated in drum channel 1212 and against drum stop surface 1220. This assembly during surgery feature is made possible by cable slot 1213 as it provides a path for cable drum 1501 to be seated in drum channel 1212 without requiring the cable lead 1101 to pass through the drum channel 1212 first.

In an alternative method, the provisional lock step using driver 600 is not performed. Once the cable is passed around the bone and through the clamp housing, the surgeon may immediately use the counter torque locker 700, with cable tensioner if she so chooses, to perform provisional or final locking.

In another alternative method, the surgeon may choose not to use a counter torque locker 700 when it is believed sufficient final locking can be achieved without it. In this method the surgeon may choose to use driver 600 with clamp housing 200 or 1200 to achieve final locking. Driver 600 may also be used with a cable tensioning device.

The foregoing invention has been described in accordance with the relevant legal standards, thus the description is exemplary rather than limiting in nature. Variations and modifications to the disclosed embodiment may become apparent to those skilled in the art and fall within the scope of the invention.

What is claimed is:

1. A counter torque locker and cable clamp for securing a surgical cable within a clamp housing comprising:
 a cable clamp housing;
 a lock of a cable fixation device;
 an elongated clamp base;
 a control arm extending from said elongated clamp base for alignment of said clamp base with said cable clamp housing;
 a cannulated worm shaft at least partially housed within said clamp base;
 said cannulated worm shaft comprising a drive boss formed thereon for engagement with the lock of said cable fixation device;
 a worm gear on said cannulated worm shaft;
 a worm rod oriented generally perpendicular to said worm shaft and at least partially housed within said clamp base;
 a worm helix on said worm rod;
 wherein said worm helix is meshed with said worm gear.

2. The counter torque locker and cable clamp of claim 1 further comprising:
 a control slot formed within said cable clamp housing;
 a control tab extending from said control arm for seating within said control slot of said clamp housing.

3. The counter torque locker and cable clamp of claim 1 further comprising:
 a drive bar;
 said drive bar disposed on said worm rod for inducing torsional forces on said worm rod.

4. A cable fixation device for securing bone segments comprising:
 a clamp housing;
 a surgical cable;
 said surgical cable having a butt;
 a drum channel situated within said clamp housing for securing said butt within said drum channel;
 a lock aperture within said clamp housing;
 a collet housed within said lock aperture;
 said collet comprising a compression gap;
 a lock cap housed within said lock aperture;
 said surgical cable formed into a cable loop with a portion of said cable residing within said collet;
 wherein central axes of said cable butt, said cable loop, said collet, and said lock cap reside in a single plane.

5. The cable fixation device of claim 4 further comprising surfaces between said lock cap and said collet that slide relative to each other for minimizing twisting of said cable when advancing said lock cap.

6. The cable fixation device of claim 4 wherein said compression gap is in the form of a top compression gap and a bottom compression gap extending from opposed ends of said collet.

7. The cable fixation device of claim 4 wherein said compression gap is open at one end.

8. A cable fixation device for securing bone segments comprising:
- a clamp housing;
- a surgical cable;
- said surgical cable having a butt;
- a drum channel situated within said clamp housing for securing said butt within said drum channel;
- a lock aperture within said clamp housing;
- a collet housed within said lock aperture;
- said collet comprising a compression gap extending from one end;
- a lock cap housed within said lock aperture;
- said surgical cable formed into a cable loop with a portion of said cable residing within said collet;
- wherein said drum channel and said lock aperture intersect and are contiguous.

9. The cable fixation device of claim 8 further comprising surfaces between said lock cap and said collet that slide relative to each other for minimizing twisting of said cable when advancing said lock cap.

10. The cable fixation device of claim 8 further comprising said cable loop orientated in a single plane.

11. The cable fixation device of claim 8 further comprising a top compression gap and a bottom compression gap extending from opposed ends of said collet for compressing said collet about said surgical cable during locking.

12. The cable fixation device of claim 8 further comprising an enlarged terminal portion at said butt of said cable and a drum stop surface positioned within said drum channel to prevent pull out of said enlarged terminal portion from within said clamp housing.

13. The cable fixation device of claim 12 wherein said enlarged terminal portion is in the form of a cable drum.

14. The cable fixation device of claim 8 wherein said clamp housing further comprises a concave bottom surface for seating adjacent to bone.

15. The cable fixation device of claim 14 further comprising a plurality of teeth projecting from said concave bottom surface for seating into bone.

16. The cable fixation device of claim 8 further comprising a pair of opposed control slots extending into each opposing side surface of said clamp housing for receiving instrumentation.

17. The cable fixation device of claim 8 wherein a drive wall of said lock cap drives against a generally flat top face of said collet for locking of said surgical cable.

18. A cable fixation device for securing bone segments comprising:
- a clamp housing;
- a collet housed within said clamp housing;
- a lock cap housed within said clamp housing;
- a surgical cable;
- a butt end of said cable secured in said clamp housing;
- said surgical cable formed into a cable loop with a portion of said cable residing within said collet and said lock cap;
- a drive wall disposed on said lock cap;
- a top face disposed on said collet;
- and surfaces between said lock cap drive wall and said collet top face that slide relative to each other for minimizing twisting of said cable when advancing said lock cap;
- wherein said top face is generally perpendicular to a long axis of said surgical cable.

19. The cable fixation device of claim 18 wherein said collet further comprises a compression gap extending from one end thereof.

20. The cable fixation device of claim 18 wherein central axes of said cable butt, said cable loop, said collet, and said lock cap reside in a single plane.

21. A cable fixation device for securing bone segments comprising:
- a clamp housing;
- a collet housed within said clamp housing;
- a lock cap housed within said clamp housing;
- a surgical cable;
- a butt end of said cable secured in said clamp housing;
- said surgical cable formed into a cable loop with a portion of said cable residing within said collet and said lock cap;
- a drive wall disposed on said lock cap;
- a top face disposed on said collet;
- and surfaces between said lock cap drive wall and said collet top face that slide relative to each other for minimizing twisting of said cable when advancing said lock cap;
- wherein said top face is generally perpendicular to a long axis of said surgical cable;
- and wherein said cable loop is oriented in a single plane.

22. A cable fixation device for securing bone segments comprising:
- a clamp housing;
- a collet housed within said clamp housing;
- a lock cap housed within said clamp housing;
- a surgical cable;
- a butt end of said cable secured in said clamp housing;
- said surgical cable formed into a cable loop with a portion of said cable residing within said collet and said lock cap;
- a drive wall disposed on said lock cap;
- a top face disposed on said collet;
- and surfaces between said lock cap drive wall and said collet top face that slide relative to each other for minimizing twisting of said cable when advancing said lock cap;
- wherein said top face is generally perpendicular to a long axis of said surgical cable;
- and further comprising a top compression gap and a bottom compression gap extending from opposed ends of said collet for compressing said collet about said surgical cable during locking.

23. A surgical cable fixation kit comprising:
- an implantable cable;
- a clamp housing;
- a lock cap for advancement into said clamp housing for locking said implantable cable;
- a collet compressible about said cable;
- a counter torque locking instrument;
- said counter torque locking instrument comprising a worm shaft for advancing said lock cap;
- said worm shaft comprising a central cannula sized to pass said implantable cable therethrough;

and a worm rod generally perpendicular to said worm shaft for transmitting torsional forces on said worm rod to said lock cap.

24. The surgical cable fixation kit of claim 23 further comprising surfaces between said lock cap and said collet that slide relative to each other for minimizing twisting of said cable when advancing said lock cap.

25. The surgical cable fixation kit of claim 23 further comprising a top compression gap and a bottom compression gap extending from opposed ends of said collet for compressing said collet about said implantable cable during locking.

* * * * *